(12) United States Patent
Brånemark

(10) Patent No.: US 6,439,887 B2
(45) Date of Patent: *Aug. 27, 2002

(54) FIXTURE, PROSTHESIS ANCHORING DEVICE AND PROSTHESIS

(75) Inventor: Per-Ingvar Brånemark, Mölndal (SE)

(73) Assignee: Medevelop AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/849,838

(22) Filed: May 4, 2001

Related U.S. Application Data

(63) Continuation of application No. 09/214,031, filed as application No. PCT/SE97/01035 on Jun. 12, 1997, now Pat. No. 6,305,398.

(30) Foreign Application Priority Data

Jun. 26, 1996 (SE) .............................................. 9602555

(51) Int. Cl.[7] .................................................. A61C 8/00
(52) U.S. Cl. ........................................ 433/173; 433/176
(58) Field of Search ................................ 433/172, 173, 433/174, 175, 176

(56) References Cited

U.S. PATENT DOCUMENTS 4,793,808 A * 12/1988 Kirsch ......................... 433/173
4,976,739 A * 12/1990 Duthie, Jr. ................... 433/174
5,575,651 A * 11/1996 Weissman .................... 433/173
5,599,185 A * 2/1997 Greenberg ................... 433/173

FOREIGN PATENT DOCUMENTS

| EP | 01266244 | * | 11/1984 |
| EP | 0370590 | * | 5/1990 |
| EP | 0466267 | * | 1/1992 |

* cited by examiner

Primary Examiner—John J. Wilson
(74) Attorney, Agent, or Firm—Ostrolenk, Faber, Gerb & Soffen, LLP

(57) ABSTRACT

The invention is related to an arrangement used to attach a prosthesis to one or more fixtures (1) anchored in a person's bone tissue. Such a fixture (1) has a fastening part (8) for the prosthesis and said fastening part has a supporting surface the prosthesis and a said fastening part has a supporting surface (9) that engages a bearing surface (13) on the prosthesis. In accordance with the first aspect of the invention such a fixture (1) on its supporting surface (9) is provided with a deformation device (18). This is plastically deformable in a direction perpendicular to supporting surface (9) to compensate for any misalignment between supporting surface (9) and bearing surface (13). In accordance with a second aspect of the invention, the deformation device is, instead, arranged on the prosthesis supporting surface (13) in a corresponding way. The invention also incorporates a prosthesis anchoring system that includes a fixture having a deformation device.

8 Claims, 4 Drawing Sheets

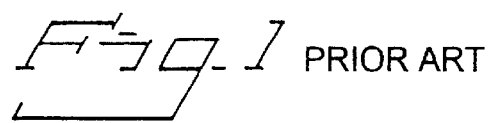
PRIOR ART
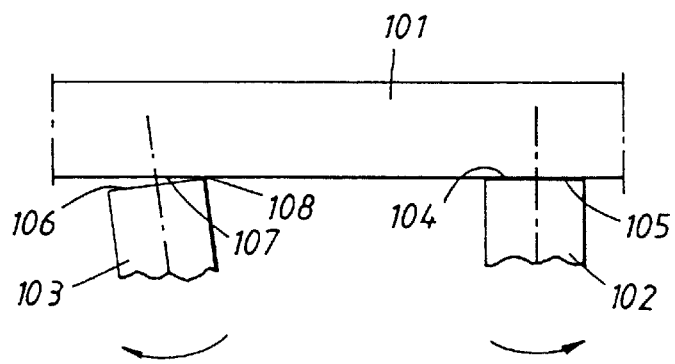
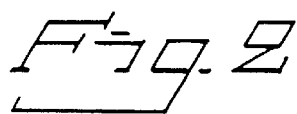
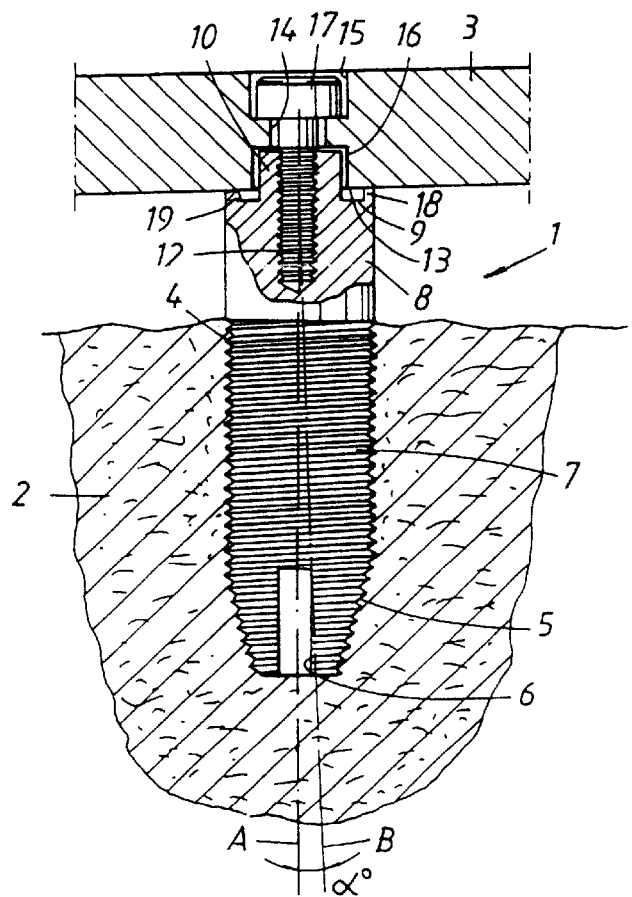

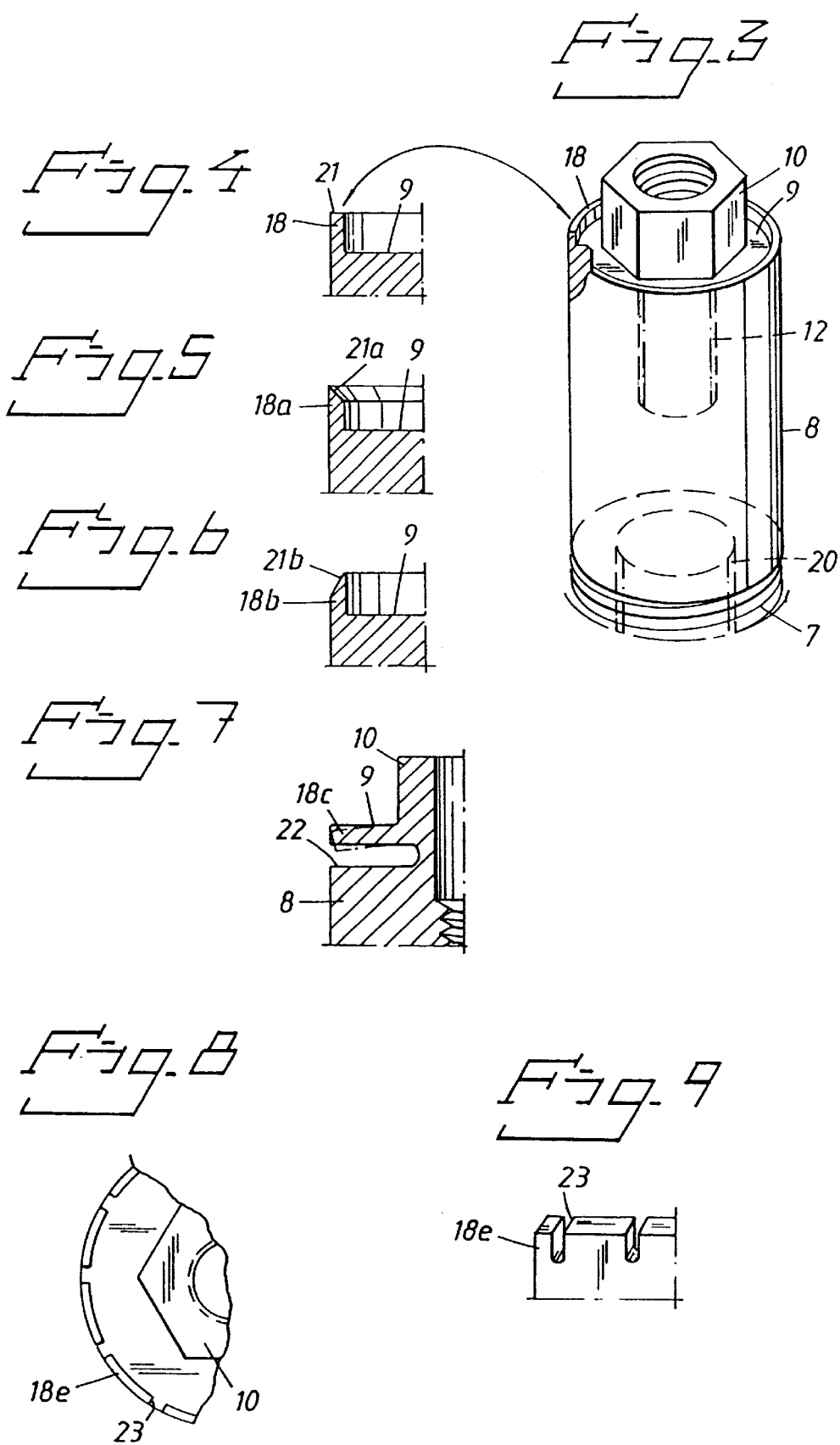

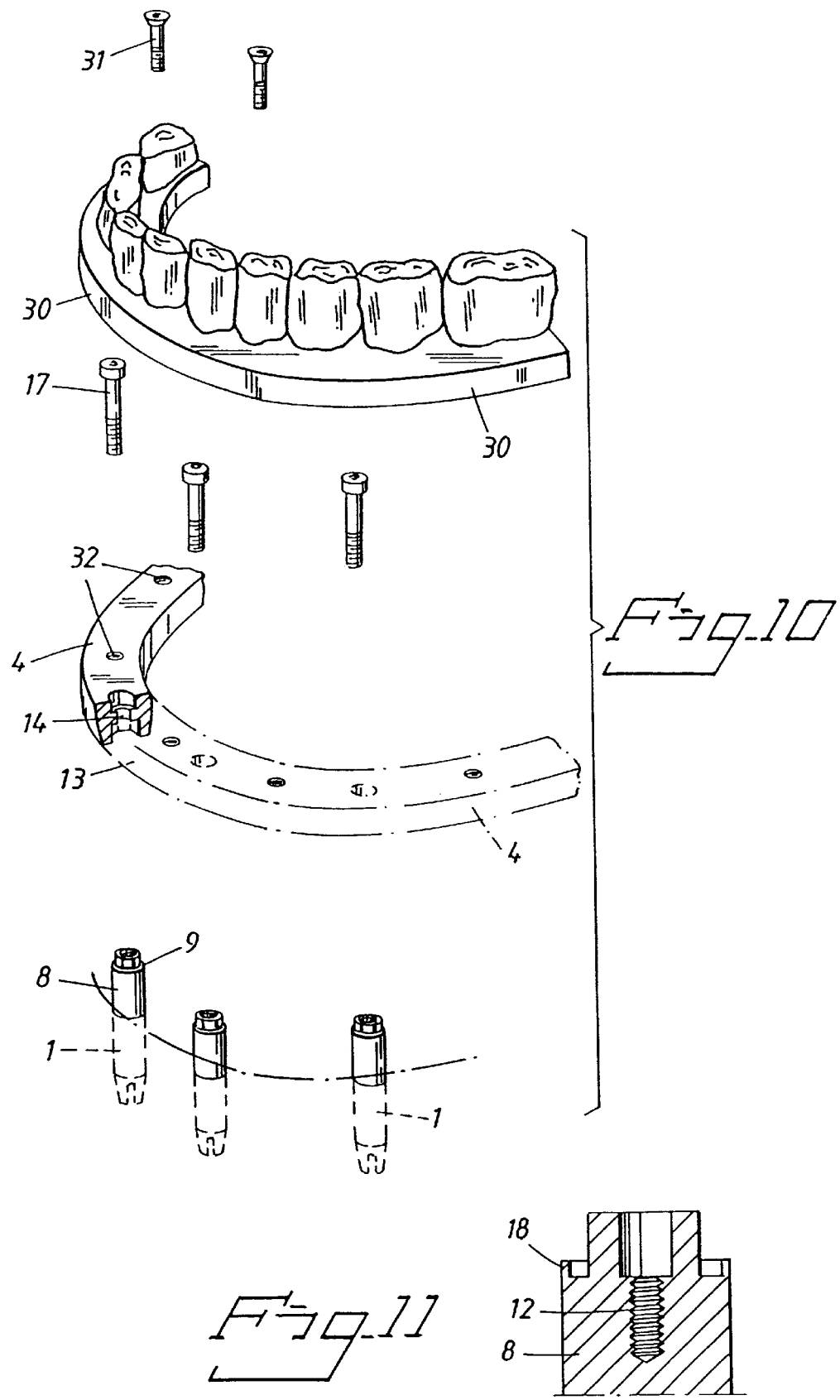

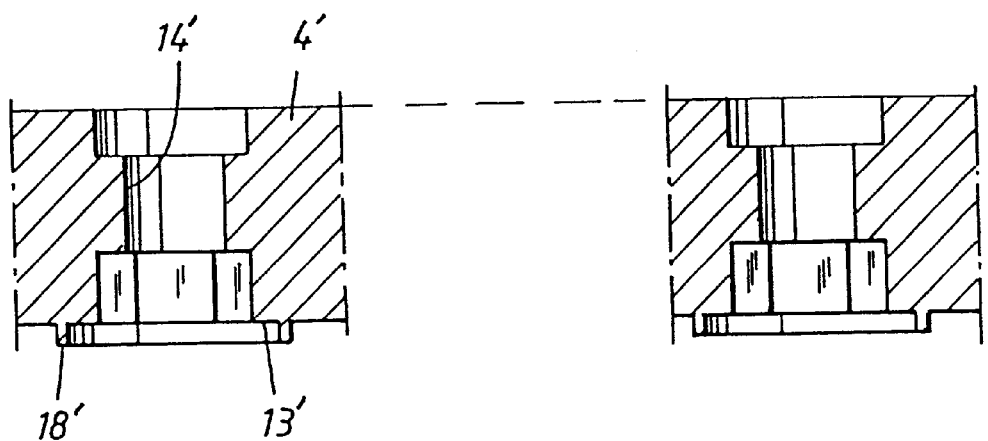
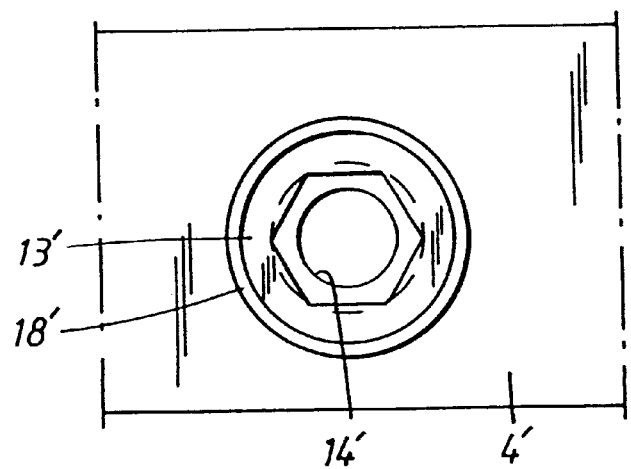

FIXTURE, PROSTHESIS ANCHORING DEVICE AND PROSTHESIS

CROSS-REFERENCE TO RELATED APPLICATIONS

This is a continuation U.S. patent application Ser. No. 09/214,031 filed Mar. 11, 1999 in the name of Per-Ingvar Brånemark entitled FIXTURE, PROSTHESIS ANCHORING DEVICE AND PROSTHESIS as the U.S. National Stage of PCT/SE97/01035 filed Jun. 12, 1997, and now U.S. Pat. No. 6,305,398.

BACKGROUND OF THE INVENTION

1. Field of the Invention

The present invention relates to a fixture for implantation and osseointegration with bone tissue whose purpose is to carry a prosthesis, a prosthesis anchoring system, and a prosthesis attached to the fixture.

2. Description of the Related Art

It is known to implant fixtures in a person's bone tissue in order to attach different types of prostheses to them, dental prostheses for example.

To make certain that the fixture anchorages are permanent, a number of factors must be fulfilled with regard to, among other things, material selections and operation techniques. In practice, fixtures developed by Professor Brånemark made of pure titanium with micro-pitted surfaces have shown very good long-term anchoring abilities. The screw-shaped fixtures are operated into a bone, the jawbone for example, and are permitted to heal in—osseointegrate—for a certain time period, usually a few months. Thereafter, a prosthesis can be mounted on the fixtures.

Most types of these fixtures are provided with external threads—and are thus implanted screws—and they are attached by screwing them into holes made in the bone tissue. The holes are often pre-threaded, but it is also possible to screw in self-tapping screws. Normally, the fixtures require shorter or longer times for healing-in before they should be exposed to significant loads. On the fixtures, one can attach different types of prostheses, and for dental prostheses one can attach individual teeth, i.e., one tooth per fixture, but it is also possible for two or more fixtures to serve as attachment points for a bridge structure containing a number of teeth or even an entire row of teeth. The fixtures are therefore designed in a suitable way at their free ends.

The free end of such a fixture to which a prosthesis is to be fastened, i.e., the fastening end, is equipped with some form of fastening device that will engage a corresponding fastening device on the prosthesis. It is herewith usual to have the attachment arranged so that a bearing surface on the prosthesis or a prosthesis-carrying element will be in contact with a supporting surface on the fixture's fastening end. The supporting and bearing surfaces should be parallel to ensure fully satisfactory functionality. This seldom poses any problem for prostheses of the type that are attached by means of only one fixture since in such cases the prosthesis, which is usually fastened by a threaded joint to the fixture, will have its bearing surface forced into contact with the fixturets supporting surface throughout its entire area when the prosthesis is screwed into place.

In many cases, a prosthesis can be anchored using more than one fixture. This is especially true in connection with jaw reconstruction when a prosthesis containing a row of teeth is to be attached, but it can also occur for prostheses used for other parts of the body.

When such a prosthesis or a holder for such a prosthesis is to be attached to two or more fixtures, the fixture onto which the prosthesis is first attached and screwed into place will force the prosthesis into a certain position as a result of the fact that its bearing surface, which is pressed against the fixture's supporting surface will forcibly have its direction determined by said supporting surface. For screwing a prosthesis to the second fixture and to additional fixtures if any, it is desirable that the corresponding bearing and supporting surfaces on this/these fixture(s) also be parallel so that there will be no misalignment. When anchoring fixtures in bone tissue one tries, of course, to have the supporting surfaces assume their intended directions relative to each other with the greatest possible precision, and these directions should be adapted to the corresponding bearing surfaces on the prosthesis. Usually the fixture surfaces are to lie in the same plane or at least be parallel.

To fully achieve this is very difficult, and it must be expected that an anchored fixture will deviate directionally from what is intended. Anchoring two or more fixtures fully parallel is also very difficult, and the possibility of obtaining precisely matching heights is remote. A deviation of even a mere degree or so results in a deficient fit between the supporting surfaces and bearing surfaces when a prosthesis, as described above, is attached to the fixtures. Since the prosthesis element or prosthesis holder is generally made from a completely rigid material such as stainless steel, a faulty fit cannot be compensated for by deforming the element or holder. Instead, there is poor contact with one or more of the fixtures' supporting surfaces and strains develop in the prosthesis structure when one tightens the threaded joint to attach the prosthesis to the fixtures. Moreover, these strains are propagated down into the bone tissue. This can cause discomfort and trouble for the patient while detracting from the functionality of the prosthesis and shortening its life expectancy.

This problem is especially common in connection with jaw reconstruction where a superstructure with a dental prosthesis is screwed in place on the fixtures directly or via an attachment bar. Such a lack of parallelism among the fixtures poses a major problem, particularly in connection with the use of prefabricated superstructures not intended for extensive individual adaptation. In order to compensate for this non-accuracy it is earlier known e.g. from EP 0126 624, EP 0370 590 and EP 0466 267 to provide an intermediate elastic device between the fixture and the prosthesis.

SUMMARY OF THE INVENTION

The present invention eliminates the disadvantages described above that are encountered when the directions of the fixtures and/or their height positions do not fully match what was intended, and without inserting special compensation elements.

In accordance with the invention, this has been achieved by means of a fixture for implantation and osseointegration with bone tissue whose purpose is to carry a prosthesis, by means of a prosthesis anchoring device having a prosthesis base that engages the fixture, and by means of a prosthesis containing a number of attachment units arranged integrally with the prosthesis or with a separate prosthesis base, where each attachment unit is arranged to be attached to a fixture anchored in a person's bone tissue, and also containing a bearing surface arranged so that when the prosthesis is attached to said fixtures, the bearing surface will be in contact with a supporting surface on the appropriate fixture, the bearing surface and the supporting surface both being substantially perpendicular to a center axis of a related fixture wherein at least one of said bearing surfaces is provided with a deformation device that is deformable in at least one direction that is perpendicular to the bearing surface to attain absolute parallelity between the supporting surface and the bearing surface when the bearing surface is pressed against the supporting surface.

Because the supporting surface on the fixture or the bearing surface on the prosthesis is integrally provided with a deformation device that can be deformed plastically in a direction perpendicular to the respective surface when misalignment occurs, the deformation device will be deformed to a corresponding extent. As a result, the bearing surface will have a fully functional contact with the supporting surface in spite of the misalignment. Since angular misalignment is absorbed by such deformation devices, the tightening of the retainer screws will not implement any strains in the patient's bone tissue.

The fixture is preferably designed with at least parts that are rotationally-symmetrical, wherewith its supporting surface is perpendicular to its center axis.

Other features and advantages of the present invention will become apparent from the following description of the invention which refers to the accompanying drawings.

In one preferable embodiment, the deformation device is designed as an axially aligned flange, suitably cylindrical and coaxial with the center axis.

It is preferred that the flange be peripherally arranged on a circular supporting surface to provide optimal deformation distribution. This will occur as a result of the fact that the flange will then be located at as long a distance as possible from the center axis.

In other preferred embodiments, the flange is provided with slots and/or is beveled axially outward, thereby facilitating deformation.

Moreover, it is preferred that the flange's outer end be pointed, i.e. sharp, thus providing progressive resistance to deformation.

The above and other preferred embodiments of the invention are set forth in the dependent claims.

BRIEF DESCRIPTION OF THE DRAWINGS

The invention is explained in greater detail in the following detailed description of the invention with reference to the accompanying figures, of which:

FIG. 1 presents a rough sketch of the known technique.

FIG. 2 is a partially sectioned side view of a fixture in accordance with a first embodiment.

FIG. 3 is a perspective view of a part of the fixture shown in FIG. 2.

FIG. 4 is an enlarged section taken through a part shown in FIG. 3.

FIGS. 5–7 are sections that correspond with what is shown in FIG. 4, illustrating the second through the fifth embodiments of the invention.

FIG. 8 is an end view of a fixture in accordance with a sixth embodiment of the invention.

FIG. 9 is a perspective view of a part shown in FIG. 8.

FIG. 10 is an exploded view of a prosthesis anchoring device in accordance with the invention.

FIG. 11 is a longitudinal section taken through a part shown in FIG. 10.

FIG. 12 is a side view of a part in a prosthesis in accordance with the invention.

FIG. 13 is an end view of a part shown in FIG. 12.

DETAILED DESCRIPTION OF EMBODIMENTS OF THE INVENTION

The purpose of FIG. 1 is to clarify the set of problems that the present invention is intended to solve, and it is therefore drawn in schematic form. 101 represents a part of a prosthesis, a bridge base for a dental bridge, for example. Prosthesis part 101 is anchored in a person's jawbone by means of a number of fixtures screwed into holes made in the jawbone. Only two fixtures 102, 103 are shown in the figure, and only their upper ends are shown. Each fixture acquires a direction determined by the hole in the jawbone in which it is anchored. Quite frequently, these holes are not fully parallel, which leads to corresponding mutual misalignment of fixtures 102, 103. Prosthesis part 101, when it is tightened against the first fixture, is forced into a position determined by the direction of the first fixture's supporting surface 104 when the corresponding bearing surface 105 on prosthesis part 101 is drawn into contact with supporting surface 104.

If, then, the second fixture 103 has an angular deviation from parallelism with the first fixture 102, the tightening of the threaded joint located at the second fixture 103 will lead to a misalignment of the second fixture's supporting surface 106 relative to the corresponding bearing surface 107 on the prostheses part so that contact will be almost of the point-to-point type, as shown at 108. When both fixtures are tightened against prosthesis part 101, torque will be developed on each fixture in the directions shown by the arrows. Such torque will create strains in the jawbone where the fixtures are anchored. The harmful effects of this are mentioned in the introduction to the description. Similar problems are encountered if the positions of the bearing surfaces of the fixtures do not match with regard to height.

FIG. 2 shows a fixture 1 according to the present invention with its anchoring end anchored in a person's lower jawbone 2. At the upper end of fixture 1, its fastening end, there is a base such as a bar 3 intended to carry a dental prosthesis bridge (not shown) attached to it.

Fixture anchoring part 7 is conventionally designed with a threaded part 4 which, at its end, has a conical part 5 provided with slots 6. Anchoring part 7, which is made of titanium, is self-tappingly screwed into a pre-drilled hole in jawbone 2. The upper end, the fastening end, of the fixture, comprises a spacer part 8 which can be combined with anchoring part 7 to form a single piece or more commonly, arranged as a separate unit that is screwed into an anchoring part 7 that has been provided with an internally threaded bore (not shown in FIG. 2).

The fastening end is provided with an attachment unit that engages another attachment unit adapted to it on bar 3, whereupon the two are attached together. The fastening end's attachment unit contains a supporting surface 9 arranged perpendicularly to the fixture's longitudinal axis A, an axially aligned projection 10 extending out from supporting surface 9, the projection having a hexagonal outer profile, and an internally threaded bore 12 in the fixture that is axially aligned relative to the top of the projection. The corresponding attachment unit for bar 3 includes a section of its bottom surface that comprises bearing surface 13, a through-going bore 14, a cylindrical countersink 15 at the upper end of the bore, a hexagonal countersink 16 at the lower end of the bore and a retainer screw 17.

Bar 3 defines a direction that is dependent on the direction of a first (not shown) fixture as described in connection with FIG. 1. As mentioned previously, an effort is made to see that normal alignment B of this direction will correspond to the shown direction A of fixture 1. Such is not the case in FIG. 1. Instead, there is an angular deviation of a° between them. A corresponding angular deviation also occurs between supporting surface 9 and bearing surface 13.

The bearing surface 9 is provided with a deformation device in the form of a flange 18 that is arranged at the periphery of bearing surface 9 and extends axially out from it. The flange is relatively thin, about 0.05 mm, and has a height of about 0.15 mm. When fixture 1 is pulled firmly onto bar 3 by tightening screw 17, the part of the fixture's supporting surface that consists of the flange will come into direct contact with bearing surface 13 on bar 3. Since the surfaces are not parallel, contact occurs initially at a single point on flange 18. Continued tightening of the screw deforms flange 18 at this location, and when the screw is tightened further, this deformation extends throughout more and more of flange 18. Because the deformation is plastic, the change in shape is retained. The left side of the figure shows the flange deformed in this way at 19. The deformed flange will acquire an end surface that is parallel with bearing surface 13 on bar 3 and contact it throughout its entire extent. Compensation has thus been obtained for angular deviation a so that there is good contact between fixture 1 and bar 3 and so that no strains develop in jawbone 2.

FIG. 3 presents a perspective view of the upper end of fixture 1. This also shows how the spacer part 8 can be attached to its anchoring part 7 by means of a threaded bore 20 represented by broken lines that engages a corresponding threaded stud-end (not shown) on spacer part 8. FIG. 3 also shows clearly how, at the upper end of spacer part 8, an axial flange 18 provided at the periphery of supporting surface 9 is shaped. This is also shown by FIG. 4, which shows a section taken through the flange and drawn to a larger scale. Flange 18 is, in this embodiment, uniformly thick and is terminated with a part that is perpendicular to the axial direction.

The embodiments shown in FIGS. 5 and 6 differ from what is shown in FIG. 4 due to the fact that the outer ends of flanges 18a and 18b are provided with bevels 21a, 21b on their inner side and outer side respectively. These bevels extend, in both cases, across the entire width of the flanges so that a pointed, i.e., sharp, edge is form at the outer end. The bevels can, of course, be arranged differently so that they extend over only a part of the width of the flange, leaving a flat edge surface at the outer end of the flange. Similarly, the flange can be provided with a bevel on both the inner and outer sides. Beveling keeps the resistance to deformation relatively low when initial contact is made. Resistance then increases more and more as the screw is tightened.

In FIG. 7, the deformation device comprises a flange 18c which is radially aligned, wherewith a radially aligned circular slot 22 around spacer part 8 separates flange 18c axially from the rest of spacer part 8. Flange 18c is deformed when pressure is brought to bear on a point farthest out on its top side, since it is then bent downward towards slot 22 as indicated by the chain lines.

In the embodiment shown in FIG. 8, flange 18e is provided with slots 23 which facilitate deformation of flange 18e. These are drawn to a larger scale in FIG. 9. Slots 23 can, as shown in FIG. 8, extend axially throughout the entire flange 18e or, as shown in FIG. 9, extend only throughout a part of its axial extent. In the latter case, a lower initial deformation resistance is obtained.

FIG. 10 presents a dental prosthesis system for which the invention's advantages are of special importance. The dental prosthesis system includes a superstructure with a bridge 30 that is provided with dental prostheses and a bar 4 to which bridge 30 is attached by means of a number of screws 31 in threaded holes 32 in bar 4. Bar 4 is anchored in a person's jawbone via three fixtures 1 to which bar 4 is attached by means of a number of screws 17, each of which is passed through a hole 14 in the bar and screwed into a threaded bore in the appropriate fixture 1. Each fixture's supporting surface 9 will come into contact with a corresponding bearing surface 13 on bar 4, and any angular deviations will be taken up, in the manner described previously, by flange 18 which is shown in FIG. 11.

FIG. 12 is a side view of a bar 4' which is of a type similar to that previously described, but it shows an alternative embodiment of the invention. Each of the individual bearing surfaces 13' is located adjacent to a fastening hole 14' on the bottom side of the bar. Each bearing surface 13' is provided with an axially aligned flange 18' that is concentric with fastening hole 14'. FIG. 13 shows, in an enlarged end view, how this flange 18' is arranged. Flange 18', in this embodiment of the invention, replaces the corresponding flange in the previously described embodiments. Here, deformation is absorbed by a deformation device on the bearing surface 13' of bar 4' instead of being taken up by such a device on the supporting surface of the fixture. In other respects, since the arrangement shown for this embodiment functions in the same way as described previously, further description is omitted. It should be understood that the deformation device shaped as flange 18' in this embodiment can be modified in the different ways set forth for the previously described embodiments in which the deformation devices are located on fixtures.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A prosthesis support fixture comprised of:
   a bone anchor;
   a prosthesis attachment part extending from one end of the bone anchor,
   the bone anchor and the prosthesis attachment part forming an elongated unitary structure having a central axis;
   the prosthesis attachment part including:
      a coupling element operative to secure a prosthesis to the fixture; and
      an integral supporting element including a planar surface substantially perpendicular to the central axis engageable with a bearing surface on a prosthesis when the prosthesis is attached to the fixture;
      the planar surface of the supporting element being plastically deformable upon contact with a bearing surface on the prosthesis while the prosthesis is being secured to the fixture by the coupling element so that the force applied by the bearing surface to the support fixture will effectively be directed along the central axis when the prosthesis is fully secured to the fixture.

2. A prosthesis support fixture as described in claim 1, in which the supporting element is comprised of an axially extending flange with an axially outer end thereof comprising the planar surface.

3. A prosthesis support fixture as described in claim 2, in which the flange includes a plurality of transverse slots.

4. A prosthesis support fixture as described in claim 1, in which the supporting element is comprised of an axially extending annular flange with an axially outer end thereof comprising the planar surface.

5. A prosthesis support fixture as described in claim 4, in which the flange includes a plurality of radial slots.

6. A prosthesis support fixture as described in claim 1, in which the supporting element is comprised of an axially extending flange having a beveled axially outer end thereof with the radially outer margin of the beveled end comprising the planar surface.

7. A prosthesis support fixture as described in claim 1, in which the supporting element is comprised of a radially extending flange having an axially outer face thereof comprising the planar surface.

8. A prosthesis support fixture as described in claim 1, further including an annular slot spaced from the axially outer end thereof, thus forming an annular flange, an axially outer face of the flange comprising the planar surface.

* * * * *